(12) United States Patent
Wisniewski

(10) Patent No.: US 10,905,581 B2
(45) Date of Patent: Feb. 2, 2021

(54) FLUID COLLECTING BAG, AN OVERFLOW DEVICE, AND A FLUID COLLECTING SYSTEM

(71) Applicant: Pawel Wisniewski, Durban (ZA)

(72) Inventor: Pawel Wisniewski, Durban (ZA)

( * ) Notice: Subject to any disclaimer, the term of this patent is extended or adjusted under 35 U.S.C. 154(b) by 577 days.

(21) Appl. No.: 15/843,037

(22) Filed: Dec. 15, 2017

(65) Prior Publication Data

US 2018/0104090 A1    Apr. 19, 2018

Related U.S. Application Data

(63) Continuation of application No. 15/119,788, filed as application No. PCT/IB2015/051296 on Feb. 20, 2015, now abandoned.

(30) Foreign Application Priority Data

Feb. 28, 2014    (ZA) .................................. 2014/01580

(51) Int. Cl.
   *A61F 5/451*      (2006.01)
   *A61F 5/44*       (2006.01)
   *A61B 10/00*      (2006.01)
(52) U.S. Cl.
   CPC .......... *A61F 5/451* (2013.01); *A61B 10/0045* (2013.01); *A61F 5/4405* (2013.01)
(58) Field of Classification Search
   CPC ........ A61B 10/0045; A61F 5/44; A61F 5/453; A61F 5/455; A61F 5/4556; A61F 5/451;

(Continued)

(56) References Cited

U.S. PATENT DOCUMENTS 3,534,738 A    10/1970   Huck
3,838,691 A    10/1974   Paludan et al.
(Continued)

FOREIGN PATENT DOCUMENTS

GB    2073595 A    10/1981

OTHER PUBLICATIONS

International Search Report & Written Opinion Issued in the PCT application, PCT/IB2015/051296, dated Jun. 15, 2015.

*Primary Examiner* — Ariana Zimbouski
(74) *Attorney, Agent, or Firm* — Gottlieb, Rackman & Reisman, P.C.

(57) ABSTRACT

This invention relates to a fluid collecting system for collecting fluid downstream from a patient via a fluid collection line. The system comprises a fluid collecting bag (12) and an overflow device (14). The bag comprises an inlet tube (20) connectable to a bladder of a patient and to the interior of the bag (18), and an overflow tube (26) connected to the inlet tube (20) adjacent a top of the bag (12) and to an optional overflow device (14) to drain the bag if overflow occurs, in use. The overflow device (14) comprises a housing (30) having chamber (32), an inlet port (34) to the chamber connectable to the overflow tube (26), and a resiliently flexible member (36) located in the chamber. The member (36) is displaceable between a storage configuration, in which the overflow member is located in the chamber (32), and a filling configuration, in which the overflow member (36) extends from the chamber with fluid received from the overflow tube (26) held therein.

19 Claims, 6 Drawing Sheets

(58) Field of Classification Search
CPC ..... A61F 5/4405; B65D 1/0292; A47K 11/06; A61G 9/006
See application file for complete search history.

(56) References Cited

U.S. PATENT DOCUMENTS

| | | | |
|---|---|---|---|
| 4,443,219 A * | 4/1984 | Meisch | A61F 5/4405 604/256 |
| 4,551,141 A | 11/1985 | McNeil | |
| 5,211,642 A | 5/1993 | Clendenning | |
| 5,711,445 A | 1/1998 | Robbins, III | |
| 5,725,515 A * | 3/1998 | Propp | A61B 5/20 600/581 |
| 6,132,407 A | 10/2000 | Genese et al. | |
| 2004/0171979 A1 | 9/2004 | O'Neil | |
| 2013/0060213 A1 * | 3/2013 | Hanuka | A61F 5/44 604/333 |

* cited by examiner

FLUID COLLECTING BAG, AN OVERFLOW DEVICE, AND A FLUID COLLECTING SYSTEM

This application is a continuation of and claims priority from U.S. application Ser. No. 15/119,788 filed Aug. 18, 2016 (published on Feb. 23, 2017 as U.S. 2017/0049605), which is the U.S. National Stage of PCT IB/2015/051296 filed Feb. 20, 2015, which in turn claims priority from South Africa Application No. 2014/01580 filed Feb. 28, 2014. This invention relates to fluid collecting bags and overflow devices therefor, particularly for medical use, for example, in urological procedures.

Certain medical procedures require the irrigation of a body cavity or organ thereafter. For example, after a urological procedure such as a trans-urethral prostate resection (TURP) procedure, there is a need for continuous irrigation of the human bladder with fluid to ameliorate clot formation from blood oozing out from a resection side of the prostate. This is provided by a system for and method of continuously irrigating the bladder with a fluid and draining of the fluid into a fluid collecting bag situated below patient level until withdrawn or drained fluids from the bladder become substantially clear of blood and/or tissue.

The fluid withdrawn or drained from the body held in the fluid collecting bag, which has a capacity of about 2 or 3 litres, is then emptied by a healthcare worker, for example, a nurse periodically or on an ad hoc basis, for example, when its maximum capacity has been reached. Failure to drain or empty the fluid collecting bag when full is problematic as this may result in a patient's bladder becoming distended with fluid. This has at least two major drawbacks in that firstly it causes pain to the patient, and secondly when the bladder is distended, irrigation stops and if a patient is bleeding from a wound there will be clot formation in the bladder. These clots may block catheters used in the irrigation procedure and if the clots are large, the patient may require a bladder washout and possibility surgical intervention.

Though regular draining of the fluid collecting bag ameliorates the above problems/drawbacks, in some cases, for example, due to understaffing at healthcare institutions this may not always be realistically possible and the fluid collecting bag is often not drained leaving the same to fill to its maximum capacity resulting in the abovementioned problems.

Some conventional methodologies and systems to address the abovementioned involve allowing overflow fluid to spill freely out of the fluid collection bags. However, these are understandably unhygienic and undesirable.

The present invention seeks at least to address the abovementioned problems and/or drawbacks.

SUMMARY OF THE INVENTION

According to a first aspect of the invention there is provided a fluid collecting bag for receiving fluid downstream from a patient via a fluid collection line or tube, the fluid collecting bag comprising:

a bag body having an interior for receiving and holding fluid;

an inlet tube comprising a first end portion in fluid communication with the interior of the bag body and a second end portion connectable in fluid communication to the fluid collection line or tube;

an outlet tube comprising a first end portion in fluid communication with the interior of the bag body and a second end portion connectable to a drainage valve for draining the interior of the bag body, in use; and an overflow tube comprising a first end portion connected in fluid communication with the inlet tube, at a region between the first and second end portions of the inlet tube, and a second end portion providing an outlet for fluid received from the first end portion, in use.

The second end portion of the inlet tube may be in fluid connection, via the fluid collection line or tube, with a catheter located in the bladder of the patient such that, in use, the fluid received in the bag body is from the bladder of the patient.

The first portion of the overflow tube may be connectable to the inlet tube at a region adjacent the first end portion of the inlet tube.

The first end portion of the inlet tube may be connectable adjacent a top portion of the bag body, and wherein the first end portion of the overflow tube may be connectable to the first end portion of the inlet tube at a region adjacent the connection of the inlet tube to the top portion of the bag body.

The first end portion of the overflow tube may be attachable transversely to the inlet tube.

The inlet tube may be connected perpendicularly to the inlet tube and hence a fluid flow path within the inlet tube so as to receive fluid therefrom in response to the bag body being substantially full of fluid, in use.

It will be appreciated that a substantial portion of the overflow tube may extend from the first end portion thereof, through the interior of the bag body, wherein the second end portion thereof protrudes or emerges from the interior of the bag body.

The overflow pipe substantially may follow an S-shaped path within the bag body with a transverse portion of the overflow pipe being located at or adjacent a meridian or middle axis of the bag body.

The overflow tube may extend exterior to the bag body.

The second end portion of the overflow tube may be connectable to an overflow device for collecting overflow fluid received from the overflow tube.

The overflow device may substantially be of the type described below.

According to a second aspect of the invention, there is provided an overflow device for use with a fluid collecting bag for receiving fluid downstream from a patient, the overflow device comprising:

a housing comprising a chamber;

an inlet port in flow communication with the chamber at a first end portion and connectable to an overflow tube from the fluid collecting bag at a second end portion for receiving overflow fluid therefrom and transmitting the same to the chamber; and a resiliently flexible or compliant and stretchable overflow member having an open end attachable to the housing in a sealing fashion and a closed end, wherein the open end of the overflow member is in fluid communication with the chamber and configured such that, in use, fluid received by the overflow member enters the chamber and causes the overflow member to be displaced between a storage configuration, in which the overflow member is located substantially within the chamber, and a filling configuration, in which the overflow member extends from the chamber with fluid held therein.

The overflow member may be in the form of a balloon or condom-like member.

The housing may comprise a circular disk-like top portion and a cylindrical wall or skirt extending from the periphery of the top portion to an end portion of the housing, wherein the chamber may be defined between the top portion and the wall of the housing.

The inlet port may be located adjacent a hub of the top portion.

The cylindrical wall may define a circumferentially extending seat adjacent the end portion of the housing for locating a circumferentially extending lip adjacent the open end of the overflow member therein.

The device may comprise a collar configured to fit around the housing, adjacent the end portion thereof, so as at least to retain the lip of the overflow member substantially in the seat.

The device may comprise a cylindrical securing member to secure the overflow tube to the inlet port of the device.

The overflow device may comprise a seal to locate and keep the overflow member in the storage configuration in the chamber.

The seal may be suitable to displace or rupture to allow the overflow member to be displaced to the filling configuration in response to a predetermined amount of fluid pressure being present in the chamber.

A non-return valve may be provided adjacent the inlet port of the overflow device so as to prevent fluid received in the overflow device to travel out of the inlet port, in use.

According to a third aspect of the invention, there is provided a fluid collecting system collecting fluid downstream from a patient via a fluid collection line, the fluid collecting system comprising:

a fluid collecting bag as hereinbefore described; and an overflow device as hereinbefore described operatively connectable, particularly in fluid communication with, to the fluid collecting bag.

According to a fourth aspect of the invention, there is provided a method of collecting fluid from a patient comprising operatively connecting a fluid collecting bag as hereinbefore described to a patient.

The method may comprise operatively attaching an overflow device as hereinbefore described to the fluid collecting bag.

DESCRIPTION OF PREFERRED EMBODIMENTS

In the following description, for purposes of explanation, numerous specific details are set forth in order to provide a thorough understanding of an embodiment of the present disclosure. It will be evident, however, to one skilled in the art that the present disclosure may be practiced without these specific details.

Furthermore, it should be pointed out that the same parts described in the different Figures are denoted by the same reference numbers and the same component names and the disclosures made throughout the description can be transposed in terms of meaning to same parts bearing the same reference numbers or same component names.

Figure 1:
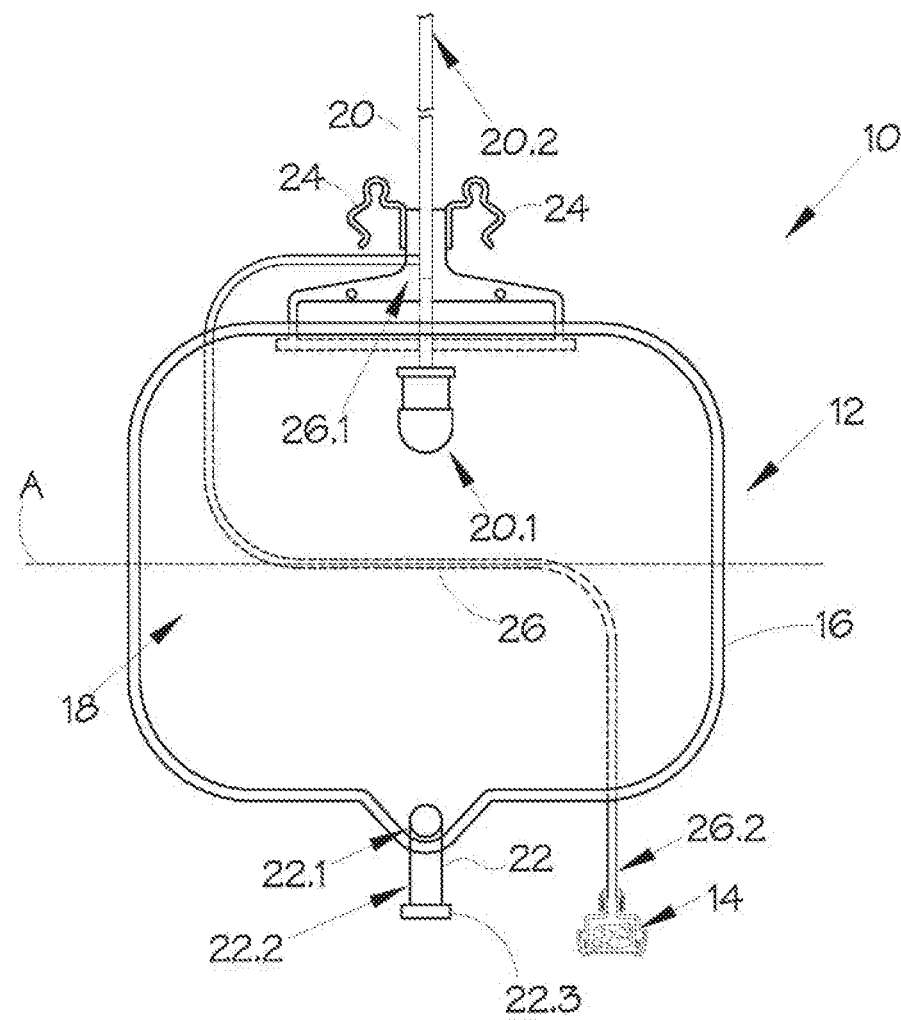
FIG. 1 shows a schematic diagram of a fluid collecting system in accordance with an example embodiment of the invention with the overflow member of the overflow device in the storage configuration.
Figure 2:
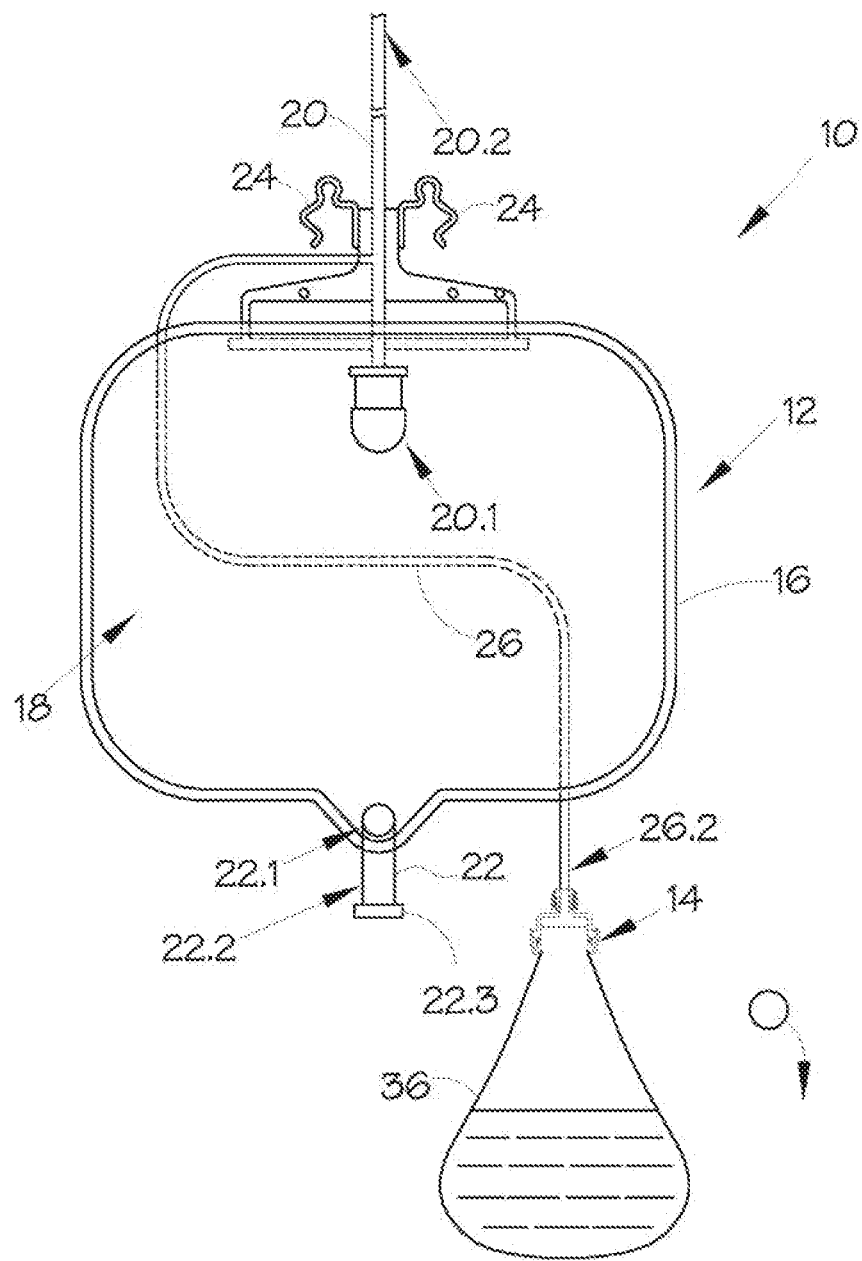
FIG. 2 shows a schematic diagram of a fluid collecting system in accordance with an example embodiment of the invention with the overflow member of the overflow device in a deployed filling configuration.

Referring to FIGS. 1 and 2 of the drawings where a fluid collecting system in accordance with an example embodiment of the invention is generally indicated by reference numeral 10.

The fluid collecting system 10 is typically used in draining or collecting fluid from a body cavity or organ of a human body, for example, during irrigation of the body cavity or organ after a medical procedure such as after a urological procedure as will be described below with reference to FIGS. 5 and 6.

The system 10 comprises a fluid collecting bag 12 and an overflow device 14 operatively connected in flow communication therewith.

The fluid collecting bag 12 comprises a bag body 16 having an interior 18 for receiving and holding fluid, in use. The bag body 16 is typically constructed from a durable plastic material used in the construction of conventional fluid collecting bags in the present field of invention. In one example embodiment, the bag body 16 may be formed in a conventional manner from at least two sheets of substantially flexible plastic sealed together adjacent peripheries thereof thereby to define the sealed or water-tight interior 18. However, it will be noted that in some example embodiments (not illustrated), the bag body 16 may define an opening adjacent a top corner thereof.

The bag 12 further comprises an inlet tube 20 comprising a first end portion 20.1 in fluid communication with the interior 18 of the bag body 16 and a second end portion 20.2 connectable in fluid communication to a fluid collection line from a catheter indwelled in the body cavity or organ of a patient as will be described below. It will be noted that the first portion 20.1 of the inlet tube 20 is connectable to a top portion of the bag body 16.

An outlet tube 22 is also provided with the bag 12, the outlet tube 22 comprising a first end portion 22.1 in fluid communication with the interior 18 of the bag body 16 and a second end portion 22.2 connectable to a drainage valve or tap 22.3 for draining the interior 18 of the bag body 16, in use in a conventional manner. The drainage valve or tap 22.3 is a conventional control valve or on/off tap operable manually to drain fluid from the interior 18 of the bag body 16.

The fluid flow through the fluid collecting bag 12 may be gravity driven the bag may be hung to a suitable support, typically below a patient, as will be described below, by way of suitable hangers 24 such that fluid travels from the inlet tube 20, located at a top of the bag 12, in use, into the interior 18 of the bag body 16 and to the outlet tube 22, located at a bottom of the bag 12, in use, under gravity. It follows that the outlet tube 22 may therefore be seen as located downstream from the inlet tube 20.

The fluid collecting bag 12 further comprises an overflow tube 26 comprising a first end portion 26.1 connected in fluid communication with the inlet tube 20, at a region between the first end portion 20.1 and second end portion 20.2 of the inlet tube 20. The overflow tube 26 also comprises a second end portion 26.2 connectable to the overflow device 14 such that, in use, fluid flows from the inlet tube 20 via the overflow tube 26 to the overflow device 14 in the event of the bag body 16, particularly the interior 18 thereof, being full of fluid as will be explained below.

In the illustrated example embodiment, the overflow tube 26 extends through the interior 18 of the bag body 16 with the second end portion 26.2 thereof protruding or emerging from the interior 18 of the bag body 16 at the bottom of the bag 12. The overflow tube 26 may run in an S-shaped pattern inside the bag body 16 and in the meridian of the bag body 16. In this way, when the bag body 16 is folded in half along the median/middle axis A of the bag body 16 (see FIG. 1), then the middle portion of the overflow tube 26 is subjected to torsion force (twisting). There is no risk of the overflow tube 26 kinking. This is an important aspect of the invention as the tube 26 is constructed of plastic (also mentioned below) which has shape memory and can stay partially occluded for a long time if folded in a particular undesirable manner which causes kinking thereof. In this way, at least the structural integrity of at least the overflow tube 26 is maintained when folding the bag body 16, for example, for packaging purposes, in use. However, in some example embodiments (not illustrated), the overflow tube 26 may extend exterior to the bag body 16.

The overflow tube 26 may be connected substantially transversely to the inlet tube 20. In a preferred example embodiment, the overflow tube 26 is connectable perpendicularly, for example, via a T-connection, to the inlet tube 20 at a region adjacent the first portion 20.1 thereof. In particular, the first portion 26.1 of the overflow tube 26 is connectable to the inlet tube 20 at a region adjacent the connection of the first portion 20.1 of the inlet tube 20 and the top of the bag body 16.

The inlet, outlet and overflow tubes 20, 22, and 26 may be of similar construction and may, for example, be constructed of a flexible plastic cylindrical tubing of a conventional type. The bag body 16 may be integrally formed with one or more of the inlet, outlet and overflow tubes 20, 22, and 26. However, in some example embodiments, one or more of the inlet, outlet and overflow tubes 20, 22, and 26 may be attached in a sealing fashion to the bag body 16. In any event, it will be appreciated that the bag body 16 is substantially sealed, especially around the inlet, outlet and overflow tubes 20, 22, and 26 so as to prevent undesirably fluid spillage.

The overflow device 14 is illustrated in part section in FIGS. 1 and 2.

It will be appreciated that though described with the overflow device 14 in accordance with the invention, it will be noted that in other example embodiments (not illustrated), the fluid collecting bag 12 may be used with other overflow devices not described herein to collect overflow fluid, for example, another receptacle optionally sealingly connected to the second end portion 26.2 of the overflow tube 26.

Figure 3:
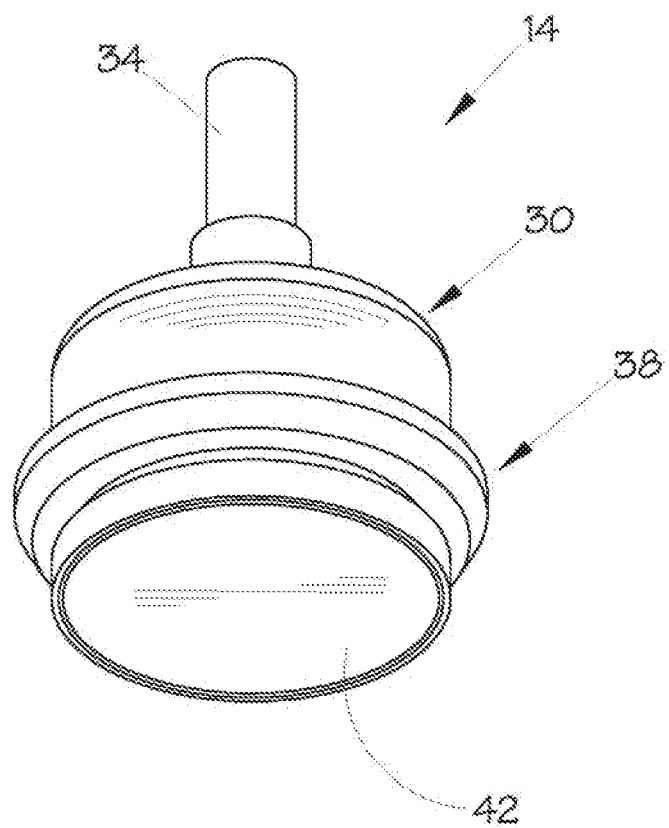
FIG. 3 shows a perspective diagram of an overflow device in accordance with an example embodiment of the invention.
Figure 4:
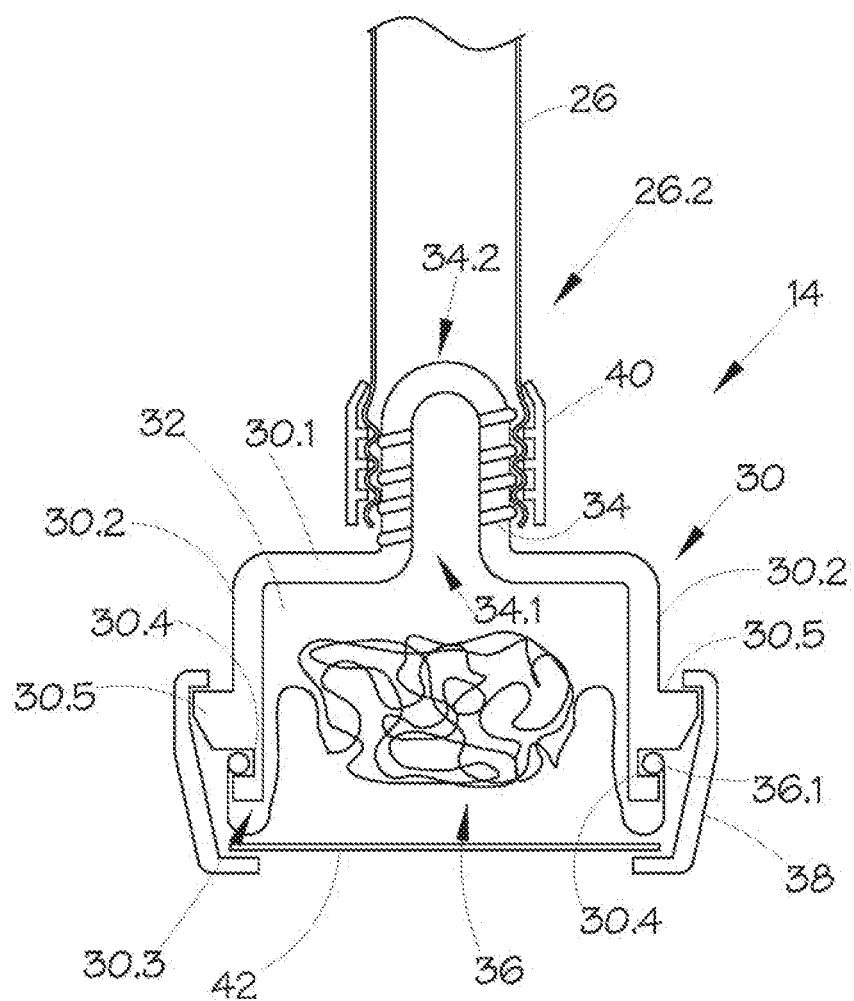
FIG. 4 shows a section though an overflow device in accordance with an example embodiment of the invention.

Reference will now be made also to FIGS. 3 and 4 of the drawings which illustrate the overflow device 14 shown in FIGS. 1 and 2 separately.

The overflow device 14 comprises a housing 30 defining a chamber 32 as can be seen more clearly in FIG. 4. In particular, the housing 30 comprises a circular disk-like top portion 30.1 and a cylindrical wall 30.2 extending from the periphery of the top portion 30.1 to an end portion of 30.3 the housing, wherein the chamber 32 has a cylindrical volume defined between the top portion 30.1 and the wall 30.2 of the housing 30.

The wall 30.2 may define a circumferentially extending seat or groove 30.4 at an outer surface thereof adjacent the end portion 30.3 of the housing 30.

The device 14 also comprises an inlet port 34 located at a hub of the top portion 30.1. The inlet port 34 is in flow communication with the chamber 32 at a first end portion 34.1 thereof and connectable to an overflow tube 26 from the fluid collecting bag 12 at a second end portion 34.2 thereof for receiving overflow fluid therefrom and transmitting the same to the chamber 32. It will be appreciated that a non-return valve may be provided adjacent the inlet port 34 to prevent fluid received thereby from travelling back to the overflow tube 26. It will be noted that in some example embodiments, the non-return valve may be provided adjacent the end portion 26.2 of the tube 26.

The overflow device 14 further comprises a resiliently flexible or compliant and stretchable overflow member 36 having a closed end and an open end comprising a circumferentially extending lip 36.1 locatable in the seat 30.4 defined by the housing 30. In this way, the member 36 is attachable to the housing 30 in a sealing fashion. The overflow member 36 is locatable within the chamber 32 in a storage configuration as shown in FIGS. 1 and 4. However, it will be noted that the overflow member 36 is displaceable to a filling configuration in which it extends from or falls out of the chamber 32, in use, as illustrated in FIG. 2.

The open end or mouth of the overflow member 36 is in fluid communication with the chamber 32 such that, in use, fluid received in the chamber 32 is received by the overflow member 36 which causes the same to be displaced between the storage configuration and the filling configuration.

To this end, the overflow member 36 is a balloon or condom-like member which may resiliently expand on receipt of fluid therein. The housing may be constructed from a hard plastic material whereas the overflow member may be constructed of rubber or latex. In some example embodiments, the overflow member 36 is a conventional latex or rubber condom having a circular lip 36.1 circumferentially extending around the mouth thereof. In any event, it will be appreciated that the member 36 needs to be very compliant and stretchable so as to be able to accommodate large amount of fluid at low pressures.

In addition to lip 36.1 of the member 36 being located in the seat 30.4 of the housing 30, to facilitate securing the member 36 to the housing 30, the device 14 may further comprise a collar 38 which may fit around the housing 30 adjacent the end portion 30.3 thereof so as at least to retain the lip 36.1 of the overflow member substantially in the seat 30.4. The collar 38 may be substantially cylindrical to engage the housing 30 at one end and allow the member 36 to fall therethrough, in use, at on opposite end thereof.

In one example embodiment, the housing may comprise a circumferentially extending protrusion 30.5 engageable with the collar 38 so as to assist in securing the collar 38 to the housing 30. The protrusion 30.5 essentially prevents axial slippage of the collar 38 from the housing 30 and the housing 38 may define complementary engaging formations to engage with the housing 30 and to prevent axial slippage from the same.

The protrusion 30.5 may be located adjacent and may be overhanging relative to the seat 30.4. In this way, it further assists in locating the lip 36.1 of the member 36 in the seat 30.4.

In yet another example embodiment, it will be noted that the collar 38 may have a slight degree of clearance from the housing 30, particularly from the member 36.1 located in the seat 30.4 so as not to frustrate operation of the member 36.

In any event, the device 14 may comprise a cylindrical securing member 40 to secure the overflow tube 26 to the inlet port 34. In this regard, the second end portion of tube 26 may fit spigot-socket fashion around the port 34 wherein the securing member 40 comprises engaging formations to secure the tube 26 to the inlet port 34. To this end, the inlet port may also comprise engaging formations on an outer surface thereof.

In a further example embodiment, the device 14 may comprise a seal 42 to locate and keep the overflow member 36 in the storage configuration.

In a preferred example embodiment, the seal 42 is in the form of a circular disk locatable in a seat defined at a base end of the collar 38. Alternately, the seal 42 may be connected to the housing 30. In any event, the disk 42 is configured to be displaceable, to allow the overflow member 36 to be displaced to the filling configuration, in response to a predetermined amount of fluid pressure being present in the chamber 32. To this end, the disk 42 may be selected to be displaced when a pressure in the chamber 32 reaches a particular predetermined threshold so that distension the bladder of a patient does not occur, in use. For example, the disk 42 may be displaced or in other words pop out of its seat when the pressure above the point of connection of the overflow tube to the inlet tube reaches a value of 25-30 cm of fluid.

In other example embodiments, the seal may be selected to rupture, to allow the overflow member 36 to be displaced to the filling configuration, in response to a predetermined amount of fluid pressure being present in the chamber 32.

In use, referring to FIGS. 1 to 4 described above, and now also in particular to FIGS. 5 and 6 when a patient 44 undergoes a urological procedure such as a TURP procedure previously mentioned, there is a need to irrigate the bladder 44.1 of said patient 44 with fluid and withdraw or drain said fluid.

In this regard, reservoirs 46 are located at a height above the patient 44, for example, suspended via suitable support means adjacent a bed of the patient 44 and a fluid supply line 48 is introduced to the bladder 44.1 of the patient 44 via conventional means, for example, through the urethra of the patient 44.

The fluid collecting bag 12 as described above is located below the patient 44 and is connected via a fluid collecting line 50 from the patient 44 in a conventional manner such that fluid from the bladder 44.1 of the patient 44 is collected or drained therefrom via the line 50 into the bag 12.

The line 50 is typically connected to the second end portion 20.2 of the inlet tube 20 such that the same is in fluid communication with the bladder 44.1 of the patient 44. To this end, the line 50 may in turn be connected to a catheter connected to the patient in a conventional fashion. In some example embodiments, it will be appreciated that the end portion 20.2 of the inlet tube 20 may comprise the line 50 and may be connected directly to the catheter.

It will be noted that one or more of the reservoirs 46, the lines 48, 50, optionally associated conventional equipment for irrigation of a body cavity, together with the fluid collecting system 10 as described herein may form part of a fluid irrigation system in accordance with an example embodiment of the invention.

Figure 5:
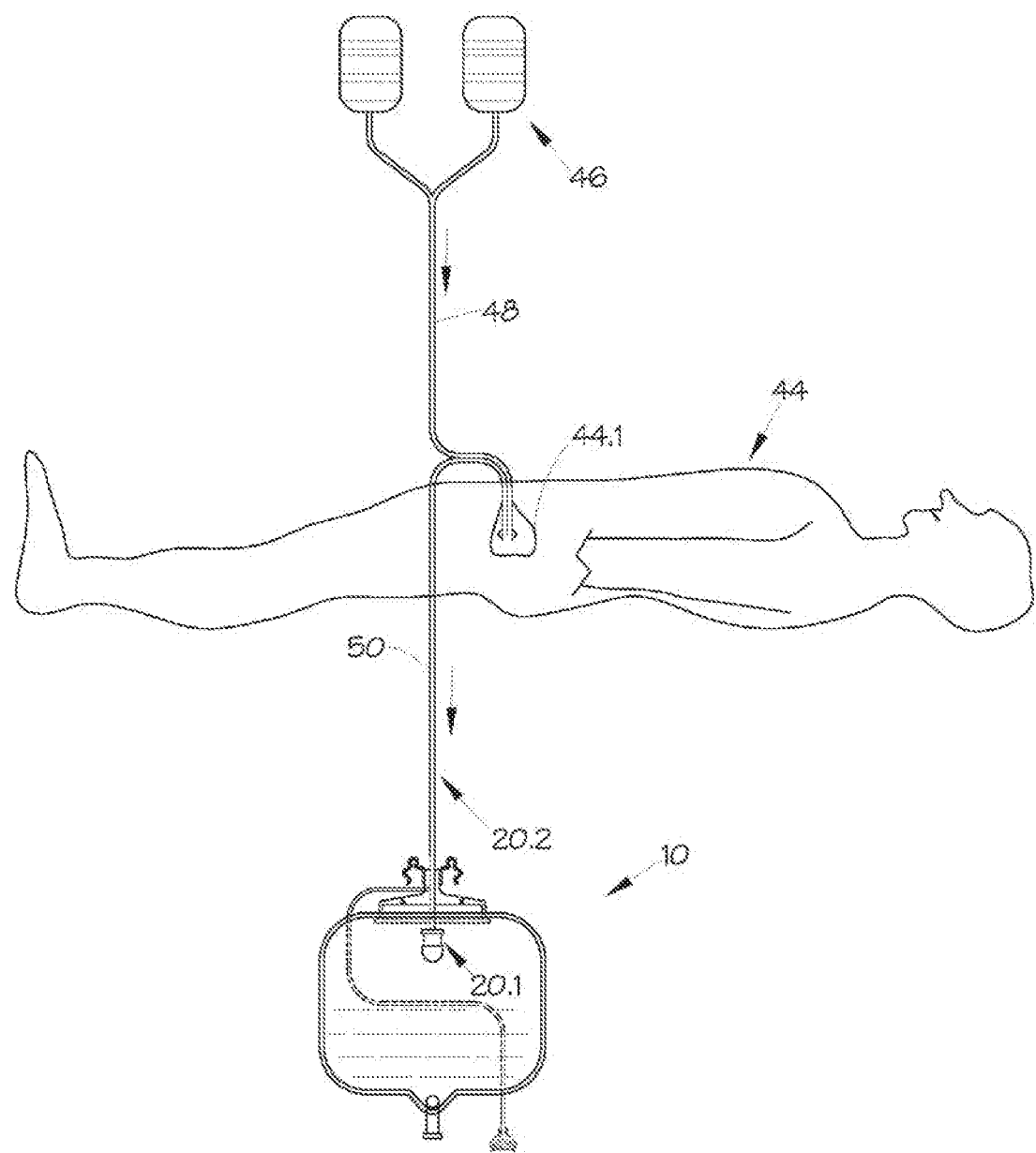
FIG. 5 shows a schematic in use diagram of a fluid collecting system in accordance with an example embodiment of the invention with the overflow member of the overflow device in the storage configuration.
Figure 6:
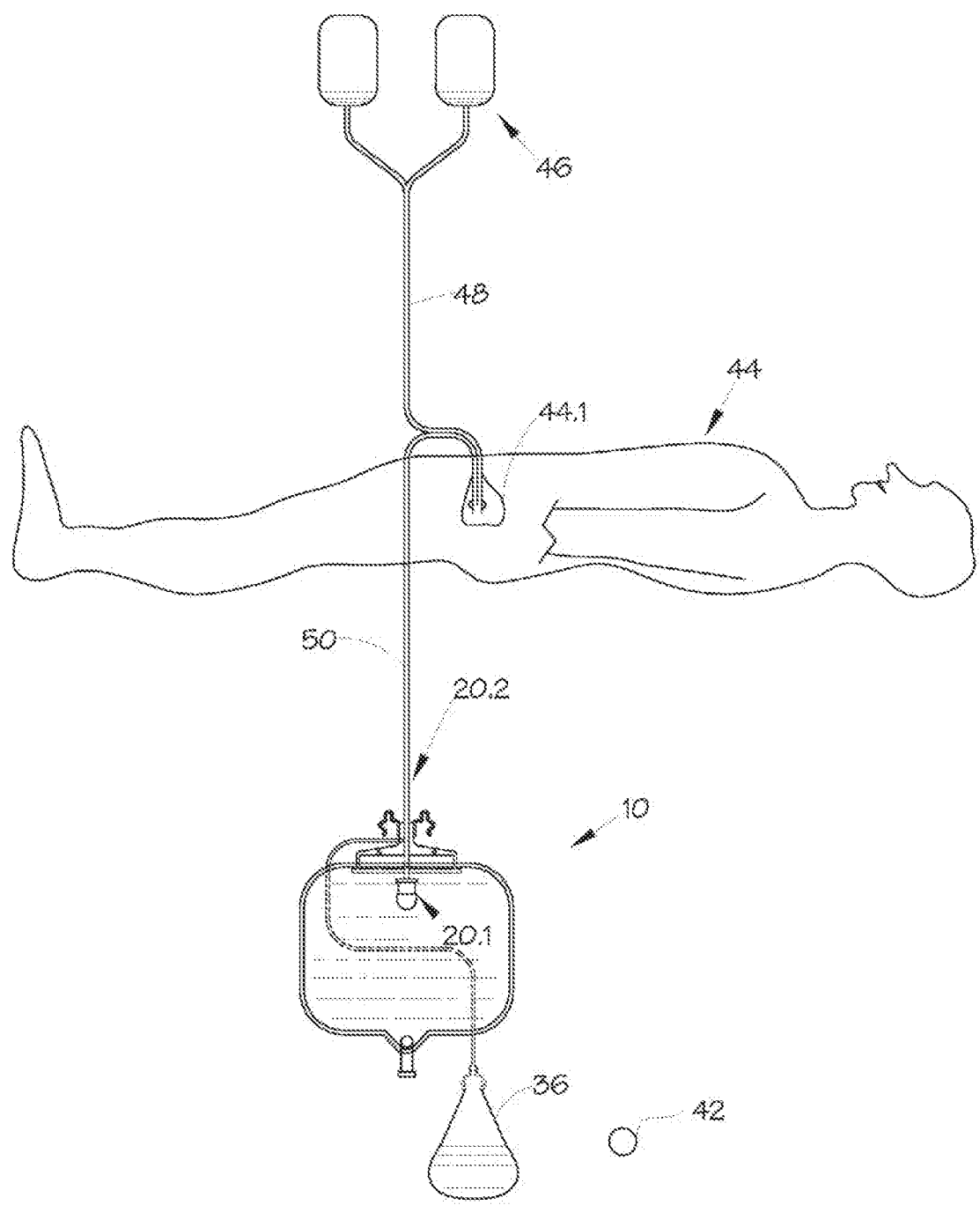
FIG. 6 shows a schematic in use diagram of a fluid collecting system in accordance with an example embodiment of the invention with the overflow member of the overflow device in the deployed filling configuration.

In any event, it will be noted that as the reservoirs 46 empty into the bladder 44.1, from being substantially full as illustrated in FIG. 5 to being substantially empty as illustrated in FIG. 6, the fluid from the bladder 44.1 is correspondingly drained in an irrigation fluid flow circuit via the line 50 into the interior 18 of the bag body 16, via the tube 20 such that the bag body 16 fills from being substantially empty as illustrated in FIG. 5 to being substantially full as illustrated in FIG. 6.

When the interior 18 of the bag body 16 is substantially full to its maximum capacity and the valve or particularly an on/off tap 22.3 is not actuated to drain the interior 18 of the bag body 16, a low pressure zone for fluid flow is formed or provided adjacent the interface between the first end portion 26.1 of the overflow tube 26 and the inlet tube 20. Overflow fluid thus flows or is drained through the tube 26 into the overflow device 14 or a suitable receptacle such as a bucket, etc.

Fluid entering the overflow device 14 via the inlet port 34 operatively connected in flow communication with a second end portion 26.2 of the overflow tube 26 enters into the chamber 32 of the device 14. Fluid entering the chamber 32 is brought into communication with the mouth of the overflow member 36 and due to either the filling of the member 36 or the pressure within the chamber 32, the seal 42 displaces by popping out of the associated seat, or in some example embodiments, ruptures allowing the closed end of the overflow member 36 to drop from the storage configuration as illustrated in FIGS. 1, 3, 4, and 5 to a filing configuration as illustrated in FIGS. 2 and 6 in which the member 36 may be filled with overflow fluid received via the overflow tube 26.

The resiliency of the member 36 allows for the same to expand thereby allowing a substantial amount of overflow fluid to be collected in the member 36.

In this way, the present invention provides a means to handle overflow fluid during irrigation of a patient. In the case of irrigating a bladder of a patient, this prevents the bladder of a patient from becoming distended which causes the problems hereinbefore described. In addition, the invention provides a hygienic manner in which to handle fluid collection during irrigation in the event of an overflow of fluid in the fluid collection bag.

The invention claimed is:

1. A fluid collecting system for assisting in receiving fluid downstream from a patient, the system including an overflow device, the device comprising:
    an overflow device housing comprising an overflow chamber;
    an overflow device inlet port in fluid communication with the overflow chamber at an overflow chamber first end portion and connectable to an overflow tube from a fluid collecting bag via a bag to overflow device fluid collection line or tube at an overflow chamber second end portion for receiving overflow fluid therefrom and transmitting the same to the overflow chamber; and
    a resiliently flexible or compliant and stretchable overflow member having an open end attachable to the overflow device housing in a sealing fashion and a closed end, wherein the open end of the overflow member is in fluid communication with the overflow chamber and configured such that, in use, fluid received by the overflow member enters the overflow chamber and causes the overflow member to be displaced between a storage configuration, in which the overflow member is located within the overflow chamber, and a filling configuration, in which the overflow member extends from the overflow chamber with fluid held therein;
    wherein the overflow device housing comprises a circular disk-like top portion and a cylindrical wall or skirt extending from the periphery of the top portion to an end portion of the housing, wherein the overflow chamber is defined between the top portion and the wall of the housing; and wherein the overflow device inlet port is located adjacent a hub of the top portion.

2. The fluid collecting system, as claimed in claim 1, wherein the overflow member is in the form of a balloon or condom like member.

3. A fluid collecting system for assisting in receiving fluid downstream from a patient, the system including an overflow device, the device comprising:

an overflow device housing comprising an overflow chamber;

an overflow device inlet port in fluid communication with the overflow chamber at an overflow chamber first end portion and connectable to an overflow tube from a fluid collecting bag via a bag to overflow device fluid collection line or tube at an overflow chamber second end portion for receiving overflow fluid therefrom and transmitting the same to the overflow chamber; and a resiliently flexible or compliant and stretchable overflow member having an open end attachable to the overflow device housing in a sealing fashion and a closed end, wherein the open end of the overflow member is in fluid communication with the overflow chamber and configured such that, in use, fluid received by the overflow member enters the overflow chamber and causes the overflow member to be displaced between a storage configuration, in which the overflow member is located within the overflow chamber, and a filling configuration, in which the overflow member extends from the overflow chamber with fluid held therein;

said fluid collecting bag designed for receiving fluid downstream from a patient via the overflow device fluid collection line or tube that selectively connects the fluid collecting bag with the overflow device, the fluid collecting bag comprising:

a bag body having an interior for receiving and holding fluid;

a bag inlet tube comprising an inlet tube first end portion in fluid communication with the interior of the bag body and an inlet tube second end portion that is selectively connectable in fluid communication to the fluid collection line or tube;

a bag outlet tube comprising an outlet tube first end portion in fluid communication with the interior of the bag body and an outlet tube second end portion selectively connectable to a drainage valve for draining the interior of the bag body; and a bag overflow tube comprising an overflow tube first end portion connected in fluid communication with the bag inlet tube, at a region between the first and second end portions of the bag inlet tube, and an overflow tube second end portion providing an outlet for fluid received from the overflow tube first end portion.

4. The fluid collecting system, as claimed in claim 3, wherein the overflow device housing comprises a circular disk-like top portion and a cylindrical wall or skirt extending from the periphery of the top portion to an end portion of the housing, wherein the overflow chamber is defined between the top portion and the wall of the housing.

5. The fluid collecting system, as claimed in claim 4, wherein the overflow device inlet port is located adjacent a hub of the top portion.

6. A fluid collecting system for assisting in receiving fluid downstream from a patient, the system including an overflow device, the device comprising:

an overflow device housing comprising an overflow chamber;

an overflow device inlet port in fluid communication with the overflow chamber at an overflow chamber first end portion and connectable to an overflow tube from a fluid collecting bag via a bag to overflow device fluid collection line or tube at an overflow chamber second end portion for receiving overflow fluid therefrom and transmitting the same to the overflow chamber; and a resiliently flexible or compliant and stretchable overflow member having an open end attachable to the overflow device housing in a sealing fashion and a closed end, wherein the open end of the overflow member is in fluid communication with the overflow chamber and configured such that, in use, fluid received by the overflow member enters the overflow chamber and causes the overflow member to be displaced between a storage configuration, in which the overflow member is located substantially within the overflow chamber, and a filling configuration, in which the overflow member extends from the overflow chamber with fluid held therein;

wherein the overflow device housing comprises a circular disk-like top portion and a cylindrical wall or skirt extending from the periphery of the top portion to an end portion of the housing, wherein the overflow chamber is defined between the top portion and the wall of the housing; and wherein the cylindrical wall defines a circumferentially extending seat adjacent the end portion of the overflow device housing for locating a circumferentially extending lip adjacent the open end of the overflow member therein.

7. The fluid collecting system, as claimed in claim 6, wherein the overflow device comprises a collar configured to fit around the overflow device housing, adjacent the end portion thereof, so as at least to retain the lip of the overflow member in the seat.

8. The fluid collecting system, as claimed in claim 1, wherein the overflow device comprises a cylindrical securing member to secure the overflow tube to the inlet port of the overflow device.

9. The fluid collecting system, as claimed in claim 1, wherein the overflow device comprises a seal to locate and keep the overflow member in the storage configuration in the overflow chamber.

10. The fluid collecting system, as claimed in claim 9, wherein the seal is suitable to displace or rupture to allow the overflow member to be displaced to the filling configuration in response to a predetermined amount of fluid pressure being present in the overflow chamber.

11. The fluid collecting system, as claimed in claim 1, wherein a non-return valve is provided adjacent the inlet port of the overflow device so as to prevent fluid received in the overflow device to travel out of the overflow device inlet port, in use.

12. The fluid collecting system, as claimed in claim 3, wherein the second end portion of the inlet tube to the fluid collecting bag is in selective fluid connection, via the fluid collection line or tube, with a catheter located in the bladder of a patient such that, in use, the fluid received in the bag body is from the bladder of the patient.

13. The fluid collecting system, as claimed in claim 3, wherein the first end portion of the bag overflow tube is connected to the bag inlet tube at a region adjacent the first end portion of the bag inlet tube.

14. The fluid collecting system, as claimed in claim 3, wherein the first end portion of the bag inlet tube is connected adjacent a top portion of the bag body, and wherein the first end portion of the bag overflow tube is connected to the first end portion of the bag inlet tube at a region adjacent the connection of the bag inlet tube to the top portion of the bag body.

15. The fluid collecting system, as claimed in claim 3, wherein the first end portion of the bag overflow tube is attachable transversely to the bag inlet tube.

16. The fluid collecting system, as claimed in claim 3, wherein a substantial portion of the bag overflow tube extends from the first end portion thereof, through the interior of the bag body, with the second end portion thereof protruding or emerging from the interior of the bag body.

17. The fluid collecting system, as claimed in claim 16, wherein the bag overflow tube follows an S-shaped path within the bag body with a transverse portion of the overflow tube being located at or adjacent a meridian or middle axis of the bag body.

18. The fluid collecting system, as claimed in claim 3, wherein the bag overflow tube extends exterior to the bag body.

19. The fluid collecting system, as claimed in claim 3, wherein the second end portion of the bag overflow tube is connectable to the overflow device for collecting overflow fluid received from the overflow tube.

\* \* \* \* \*